United States Patent
Ahlering et al.

(10) Patent No.: US 8,653,057 B1
(45) Date of Patent: Feb. 18, 2014

(54) PROPHYLACTIC PERIOPERATIVE TESTOSTERONE SUPPLEMENTATION FOR PROTECTION OF AND RECOVERY OF FUNCTION

(75) Inventors: Thomas E. Ahlering, Laguna Niguel, CA (US); Douglas Skarecky, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 373 days.

(21) Appl. No.: 13/194,865

(22) Filed: Jul. 29, 2011

Related U.S. Application Data

(60) Provisional application No. 61/369,646, filed on Jul. 30, 2010.

(51) Int. Cl.
*A61K 31/56* (2006.01)

(52) U.S. Cl.
USPC .......................................... 514/182; 514/170

(58) Field of Classification Search
USPC .................................................. 514/170, 182
See application file for complete search history.

(56) References Cited

PUBLICATIONS

Rhoden et al., New England Journal of Medicine, 2004;350:482.*
Morgentaler, Curr Treat Options Oncol, 2006;7:363-369.*
Khera et al., J Sex Med 2009;6:1165.*

* cited by examiner

*Primary Examiner* — San-Ming Hui
(74) *Attorney, Agent, or Firm* — Venable LLP; Stefan J. Kirchanski

(57) ABSTRACT

Testosterone levels in a patient predicts whether or not the patient is likely to recover sexual potency following radical prostatectomy. Lower levels of testosterone are associated with a lower rate of potency recovery and with more aggressive prostate cancers. Therapeutically increasing circulating testosterone leads to improved rates of return to potency.

9 Claims, 1 Drawing Sheet

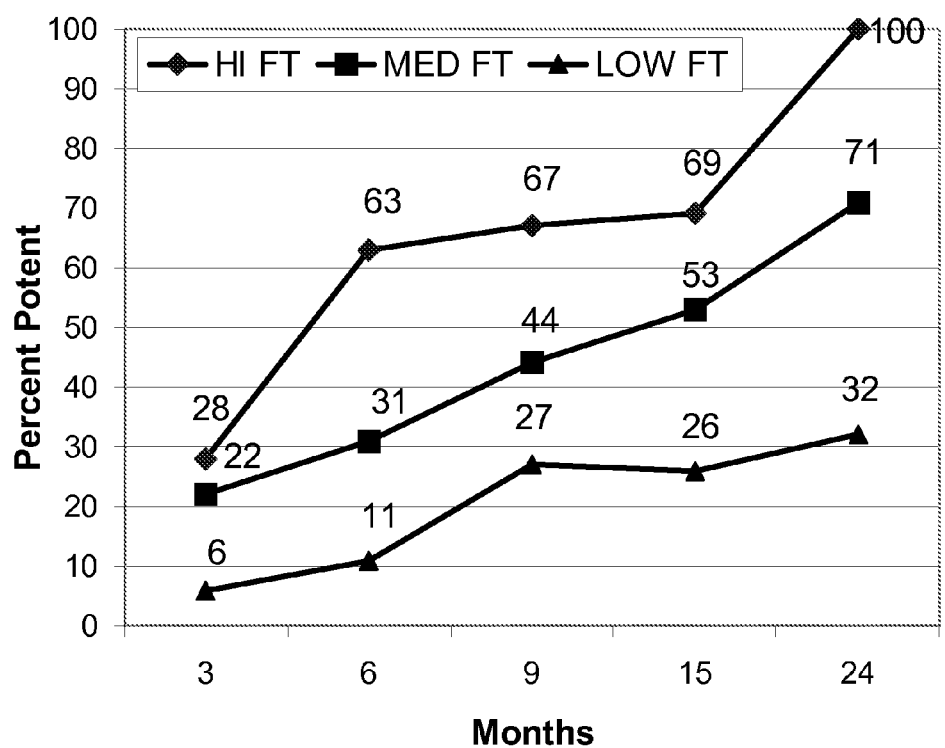

PROPHYLACTIC PERIOPERATIVE TESTOSTERONE SUPPLEMENTATION FOR PROTECTION OF AND RECOVERY OF FUNCTION

CROSS-REFERENCE TO PRIOR APPLICATIONS

The present application is the non-provisional version of U.S. Provisional Patent Application No. 61/369,646 (filed 30 Jul. 2010 and incorporated herein by reference) and claims benefit of and priority from that application.

U.S. GOVERNMENT SUPPORT

Not applicable.

BACKGROUND OF THE INVENTION

1. Area of the Background

This invention is generally in the area of urology and more specifically in improved treatment and outcome for radical prostatectomy surgery.

2. Description of the Background

Low testosterone level ("andropause", androgen deficiency of the aging male [ADAM] or hypogonadism) has an estimated prevalence of 2 to 4 million men in the United States of which only 5% receive treatment. [1] Testosterone deficiency can be linked to premature mortality and to a number of systemic diseases such as sexual disorders, diabetes, cardiovascular disease and metabolic syndrome. [2] Symptoms include decreased libido, depression, decreased muscle mass and bone density, anemia and lack of energy. [3] Total testosterone starts to decrease at age 40 years at a rate of approximately 1% (3.2 ng/dl) per year. [4] Mulligan et al. found the prevalence of hypogonadism was 38.7% in men 45 years and older presenting to primary care offices. [5] In addition to general health issues we have also confirmed earlier publications for an oncological effect. Our data (discussed below) confirm earlier reports that lower androgen levels are associated with higher grade Prostate Cancers which have a greater risk of extraprostatic extension and positive surgical margins.

In 1941, Huggins and Hodges showed that removal of the testicles (which are the primary sources of testosterone) resulted in regression of prostate cancer. [9] Since that report it has been considered taboo to offer men with history of prostate cancer any form of testosterone supplementation because of concerns such supplementation would result in recurrence of disease. [10] Although the majority of prostate cancer patients treated with local therapy is cured, approximately 15% to 40% will experience a biochemical PSA recurrence. [19 and 20] However, several recent clinical studies have shown testosterone replacement in men after a radical prostatectomy increased testosterone levels without increasing prostate specific antigen (PSA). [11, 12 and 13] These studies in effect challenge the idea that testosterone replacement is unsafe in men with low testosterone and a history of radical prostatectomy for prostate cancer. However, it should be kept in mind that these studies are based on small numbers of men (7, 10 and 57) and over short time periods (13 and 19 months).

Thus, the U.S. Food and Drug Administration continues to mandate that testosterone package inserts state that testosterone is contraindicated in men who have a history of prostate cancer. [17] The 2002 Third International Consensus Consultation on Prostate Cancer recommends that patients with prostate cancer never receive testosterone supplementation because of the fear that testosterone replacement therapy following a radical prostatectomy might promote recurrence from residual prostate cancer. [18]

Testosterone supplementation may also have side effects such as overproduction of red blood cells which could lead to clotting problems, liver problems, and exacerbation of sleep apnea as well as side local effects at the site of administration.

Nevertheless, testosterone supplementation has been shown to counteract the negative effects of testosterone deficiency by enhancing sexual function, reversing depression, increasing bone mineral density and fat-free body mass, stimulating production of red blood cells and improving strength, energy, cognition and mood. [6-8] The studies mentioned above demonstrate that the use of testosterone supplementation is not associated with recurrence of prostate cancer. In fact, low testosterone is associated with an increased risk of prostate cancer [14] and with more aggressive and higher grade prostate cancer. [15] In addition, PSA values have not been shown to increase significantly after testosterone replacement therapy. [16]

SUMMARY OF THE INVENTION

We have discovered and documented unexpected trends of low androgen levels in patients undergoing RARP (robot-assisted radical prostatectomy) for prostate cancer. In summary, both Total Testosterone (TT) and Free Testosterone (FT) are important markers that impact men with prostate cancer in the age range of ~40 to 80 years. We have discovered that low levels of these androgens impact general health issues negatively in the following ways: increased BMI (body mass index), increased weight without impact on height, increased prostate weight and decreased hemoglobin. In general there appears to be a trend that the lower the androgen levels the greater impact. We have also seen what appears to be threshold levels for some parameters such as Urinary quality of life (men with TT <200 have significantly higher AUAs [American Urological Association] and Bother scores—the most accepted "validated" tools for assessing urinary symptoms) and sexual function (as assess by the Sexual Health Inventory for Men 9SHIM] score). Most important our data demonstrate improved potency recovery after prostatectomy with FT levels above 5.1 ng/ml. In fact our data suggests that higher testosterone levels results in quicker and more complete recovery. Not only are testosterone levels predictive of outcome but also based on our findings as well as a significant literature supporting the neuroprotective properties of testosterone, we support the benefit of increasing TT and FT levels preoperatively and for 3 months postoperatively. Our results support the impact of androgens as being neuroprotective in general and for the cavernous nerves in particular.

DESCRIPTION OF THE FIGURES

FIG. 1 is a chart relating the level of Free Testosterone to return of potency following prostatectomy.

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a method based on FT levels of predicting outcome of prostatectomy and a method of modulating outcome by testosterone supplementation Pelvic surgeries such as those dealing with the urogenital system may have more or less pronounced side effects. For example, the relatively common radical prostatectomy (either traditional open prostatectomy or robot-assisted radical prostatectomy [RARP]) can have a variety of side effects. Following prostate surgery the patient often experiences temporary or even prolonged-permanent difficulties with urinary incontinence. In addition, prostate surgery frequently results in minor to profound sexual dysfunction. This is not surprising because male sexual functioning relies on an interaction between the nervous system, the endocrine system and the circulatory system. The pelvic region is a plexus of many nerves, and nerve fibers may be severed or damaged during prostate surgery. Furthermore, removal of the prostate traumatizes surrounding neuromuscular tissues causing inflammation and subsequent dysfunction. As a result, increasingly sophisticated and relatively non-invasive prostate surgeries have been developed to "spare nerves." Many of these procedures involve microscopic robotic surgeries. With these techniques one can demonstrate that few if any nerves are actually severed. Nevertheless, these surgeries continue to result in significant impotence in patients due to stretching of the nerves (traction injury) as well as inflammatory damage resulting in dysfunction of surrounding structures.

We have discovered an unexpected relationship between the male sex hormone testosterone and immunity to and/or recovery from the damage caused by prostatectomy. It is well-known that testosterone is responsible for development of male secondary sexual characteristics and for proper functioning of the entire male reproductive system. Thus, it is not surprising that significant testosterone deficiency often leads to impotency. But it is surprising that testosterone levels are surprisingly good predictors of impotency (or lack thereof) resulting from prostate surgery (and probably from any other surgery or trauma to the male urogenital system). Further, supplementation of testosterone can ameliorate loss of potency either by limiting damage or by speeding the healing process.

When we examined Total Testosterone (TT) and Free Testosterone (FT) levels in patients undergoing RARP to see if lowered levels of testosterone impact recovery of sexual function. Prospective data were gathered for men undergoing RARP by a single surgeon (N=149) so as to control for any surgical variations. Recent postoperative TT levels and sex hormone binding globulin (SHBG) were used to calculate FT. The study group included men (40-78 years) with preoperative International Index of Erectile Function-5 (IIEF-5) scores of 15-25. Potency was defined as two affirmative answers to "erections adequate for penetration" and "were the erections satisfactory" using self administered validated questionnaires (SHIM).

Table 1A shows the relationship between physical characteristics of the 149 patients and the TT scores for those patients. In an attempt to get at possible correlations the data have been stratified into four different groups. The TT data range from 100 to 850 ng/dl. The high/low division point is made at either 200, 250, 300 or 350 ng/dl. The table shows weight (in pounds), height (in inches), BMI, pre-operation PSA (prostate-specific antigen in ng/ml of blood), pre-operation hemoglobin (g/dl) and total prostate weight (g). In each group the measurement for the high group is compared to the low group and statistical significance is given. If the p-value is at or below 0.1, the difference is considered statistically significant. The dividing point for the stat stratification affects apparent statistical significance. For weight there is a trend for individuals having a higher weight to have a lower TT level. In most of the stratified groups this difference is statistically significant (shaded). On the otherhand, height of the subjects does not appear to be related to TT. However, BMI which is calculated from height and weight does show a significant relationship with lower TT individuals have a higher BMI. PSA level which is often used to detect the presence of prostate cancer does not show a significant relationship to TT nor does the level of hemoglobin in the blood (administration of excess testosterone usually causes the level of hemoglobin to increase. There is, however, a consistent trend in prostate weight where low TT individuals show an increase in prostate weight.

TABLE 1A

|  | Samples | TT group | Wt (lb) | Ht (in) | BMI | Pre-PSA | Pre-Hgb | Prost Wt |
|---|---|---|---|---|---|---|---|---|
| TT- | 138 | 200-850: | 189.7 | 70.2 | 27.0 | 6.8 | 15.0 | 53.5 |
| (hi, low@200): | 11 | 100-199: | 209.0 | 71.2 | 28.9 | 5.3 | 15.0 | 55.5 |
|  | Total: 149 | p-value: | 0.03 | 0.21 | 0.08 | 0.36 | 0.73 | 0.73 |
| TT- | 120 | 250-850: | 189.0 | 70.2 | 26.8 | 6.6 | 15.1 | 53.0 |
| (hi, low@250): | 29 | 100-249: | 199.9 | 70.4 | 28.3 | 7.1 | 14.8 | 56.3 |
|  | Total: 149 | p-value | 0.07 | 0.71 | 0.05 | 0.63 | 0.19 | 0.40 |
| TT- | 101 | 300-850: | 188.7 | 70.2 | 26.8 | 6.2 | 15.1 | 51.8 |
| (hi, low@300): | 48 | 100-299 | 196.2 | 70.4 | 27.7 | 7.7 | 14.9 | 57.5 |
|  | Total: 149 | p-value: | 0.14 | 0.56 | 0.13 | 0.13 | 0.17 | 0.08 |
| TT- | 76 | 351-850: | 185.1 | 70.1 | 26.4 | 6.2 | 15.2 | 50.9 |
| (hi, low@350): | 73 | 100-350: | 197.4 | 70.5 | 27.8 | 7.2 | 14.8 | 56.4 |
|  | Total: 149 | p-value: | 0.01 | 0.25 | 0.01 | 0.24 | 0.03 | 0.07 |

Table 2A shows a similar data analysis for FT. For this parameter the measurements ranged from 2-12 ng/dl. The high/low division was made at 4.9, 5.1, 5.3 or 6.0 ng/dl. Again, there is a trend for weight to be negatively related to FT value but this relationship is statistically significant for only the 4.9 division group. Height is not significantly related to FT level nor is BMI (although there is a weak trend for low FT individuals to show an increased BMI). With hemoglobin levels there is a trend for higher FT individuals to show higher hemoglobin levels. Again, there is a statistically significant relationship between larger prostates and low testosterone (FT).

TABLE 2A

|  | Samples | FT group | Wt (lb) | Ht (in) | BMI | Pre-PSA | Pre-Hgb | Prost Wt |
|---|---|---|---|---|---|---|---|---|
| FT- | 115 | 4.9-12: | 188.7 | 70.1 | 26.9 | 6.4 | 15.1 | 52.0 |
| (hi, low@4.9): | 34 | 2-4.9: | 199.4 | 70.9 | 27.8 | 7.7 | 14.9 | 59.2 |
|  | Total: 149 | p-value: | 0.06 | 0.07 | 0.22 | 0.23 | 0.25 | 0.05 |
| FT- | 106 | 5.1-12: | 189.9 | 70.2 | 27.0 | 6.5 | 15.1 | 51.4 |
| (hi, low@5.1): | 43 | 2-5.09: | 194.2 | 70.6 | 27.3 | 7.2 | 14.9 | 59.0 |
|  | Total: 149 | p-value: | 0.41 | 0.38 | 0.62 | 0.47 | 0.19 | 0.02 |
| FT- | 100 | 5.3-12: | 189.7 | 70.2 | 27.0 | 6.4 | 15.1 | 51.4 |
| (hi, low@5.3): | 49 | 2-5.3: | 194.1 | 70.4 | 27.4 | 7.3 | 14.9 | 58.1 |
|  | Total: 149 | p-value: | 0.39 | 0.56 | 0.45 | 0.33 | 0.15 | 0.04 |
| FT- | 78 | 6-12: | 190.9 | 70.3 | 27.1 | 6.0 | 15.1 | 51.1 |
| (hi, low@6): | 71 | 2-6: | 191.4 | 70.3 | 27.2 | 7.4 | 14.9 | 56.3 |
|  | Total: 149 | p-value: | 0.92 | 0.93 | 0.83 | 0.10 | 0.24 | 0.09 |

Table 1B shows the relationship between TT and FT and age and urological/sexual health factors as stratified according to TT in the same manner as Table 1A. There is a weak association between TT and age, and a considerable trend in AUA rating and TT level with low TT being associated with higher (less satisfactory) AUA scores. There is also relationship between higher Bother scores and low TT in the 200 ng/dl grouping. Sexual health is negatively related to TT scores in the 200 ng/dl and 250 ng/dl groupings.

Finally, Table 1C shows the TT groups as related to factors that measure the aggressiveness of the prostates cancer. The total Gleason Score (GS tot) represents the sum of the Gleason Score for both primary and secondary cancers. The GS is an estimation of the abnormal/disorganized nature of the cells. The score ranges from 1 to 5 (with 5 being highly abnormal). Thus, the GS total can potentially be as high a 10. The GS for the primary lesion can range between 1 and 5. The greater the GS, the more abnormal the cancer cells and gen-

TABLE 1B

|  | Samples | TT group | TT | FT | Age | AUA | Bother | SHIM |
|---|---|---|---|---|---|---|---|---|
| TT- | 138 | 200-850: | 382.3 | 6.7 | 61.1 | 7.5 | 1.5 | 20.4 |
| (hi, low@200): | 11 | 100-199: | 160.5 | 3.6 | 62.5 | 11.4 | 2.5 | 18.5 |
|  | Total: 149 | p-value: |  |  | 0.55 | 0.05 | 0.02 | 0.33 |
| TT- | 120 | 250-850: | 405.2 | 7.0 | 61.1 | 7.5 | 1.6 | 20.6 |
| (hi, low@250): | 29 | 100-249: | 203.2 | 4.3 | 61.6 | 8.9 | 1.7 | 18.9 |
|  | Total: 149 | p-value: |  |  | 0.79 | 0.30 | 0.59 | 0.23 |
| TT- | 101 | 300-850: | 429.7 | 7.2 | 61.7 | 7.4 | 1.6 | 20.4 |
| (hi, low@300): | 48 | 100-299: | 231.7 | 4.8 | 60.0 | 8.6 | 1.6 | 20.0 |
|  | Total: 149 | p-value: |  |  | 0.21 | 0.31 | 0.98 | 0.72 |
| TT- | 76 | 351-850: | 462.1 | 7.6 | 61.2 | 7.5 | 1.7 | 20.6 |
| (hi, low@350): | 73 | 100-350: | 265.7 | 5.2 | 61.2 | 8.0 | 1.5 | 20.0 |
|  | Total: 149 | p-value: |  |  | 0.98 | 0.63 | 0.65 | 0.61 |

Table 2B shows these same factors for FT. With the FT measurements the relationship between increasing age and decreasing FT is apparent. There is a weak association of higher AUA scores with lower FT, but the Bother scores do not appear to be at all correlated with FT. On the otherhand, higher SHIM scores appear to correlate with higher FT levels.

erally the more aggressive the cancer. T3 and t2 are tumor grades that reflect how advanced a given cancer is. T3 cancers are larger and have begun to penetrate the prostate capsule. Because this is expressed as a ration of t3/t2, the larger the score, the more advanced the cancer. Finally, margins are a measurement of whether abnormal cells are found at the

TABLE 2B

|  | Samples | TT group | TT | FT | Age | AUA | Bother | SHIM |
|---|---|---|---|---|---|---|---|---|
| TT- | 138 | 200-850: | 382.3 | 6.7 | 61.1 | 7.5 | 1.5 | 20.4 |
| (hi, low@200): | 11 | 100-199: | 160.5 | 3.6 | 62.5 | 11.4 | 2.5 | 18.5 |
|  | Total: 149 | p-value: |  |  | 0.55 | 0.05 | 0.02 | 0.33 |
| TT- | 120 | 250-850: | 405.2 | 7.0 | 61.1 | 7.5 | 1.6 | 20.6 |
| (hi, low@250): | 29 | 100-249: | 203.2 | 4.3 | 61.6 | 8.9 | 1.7 | 18.9 |
|  | Total: 149 | p-value: |  |  | 0.79 | 0.30 | 0.59 | 0.23 |
| TT- | 101 | 300-850: | 429.7 | 7.2 | 61.7 | 7.4 | 1.6 | 20.4 |
| (hi, low@300): | 48 | 100-299: | 231.7 | 4.8 | 60.0 | 8.6 | 1.6 | 20.0 |
|  | Total: 149 | p-value: |  |  | 0.21 | 0.31 | 0.98 | 0.72 |
| TT- | 76 | 351-850: | 462.1 | 7.6 | 61.2 | 7.5 | 1.7 | 20.6 |
| (hi, low@350): | 73 | 100-350: | 265.7 | 5.2 | 61.2 | 8.0 | 1.5 | 20.0 |
|  | Total: 149 | p-value: |  |  | 0.98 | 0.63 | 0.65 | 0.61 | margins of the resected tissue. The higher the number, the more advanced the cancer. GS total shows a weak negative association with TT (higher TT values having higher GS tot scores). The GS of the primary tumor shows a stronger negative correlation with TT (lower TT being associated with higher GS. Similarly, the t3/t2 values are increased with lower TT. This is also shown with Margins where lower TT values are more likely to higher margin scores.

The overall picture is that lower testosterone values (measure as either TT or FT) are associated with negative factors including BMI, prostate size and extent and aggressiveness of the prostate cancer. In some instances these factors seem more closely correlated to FT than to TT. These data show that conventional wisdom about testosterone making prostate cancer worse may be somewhat misguided.

TABLE 1C

|  | Samples | TT group | GS: tot | GS: prim | t3 vs t2 | MARGINS |
|---|---|---|---|---|---|---|
| TT- | 138 | 200-850: | 7.0 | 3.3 | 0.3 | 0.1 |
| (hi, low@200): | 11 | 100-199: | 7.4 | 3.5 | 0.5 | 0.2 |
|  | Total: 149 | p-value: | 0.13 | 0.17 | 0.24 | 0.44 |
| TT- | 120 | 250-850: | 7.0 | 3.3 | 0.3 | 0.1 |
| (hi, low@250): | 29 | 100-249: | 7.2 | 3.5 | 0.4 | 0.2 |
|  | Total: 149 | p-value | 0.26 | 0.04 | 0.29 | 0.24 |
| TT- | 101 | 300-850: | 7.0 | 3.3 | 0.3 | 0.1 |
| (hi, low@300): | 48 | 100-299: | 7.1 | 3.5 | 0.3 | 0.2 |
|  | Total: 149 | p-value: | 0.28 | 0.01 | 0.80 | 0.14 |
| TT- | 76 | 351-850: | 7.0 | 3.3 | 0.2 | 0.1 |
| (hi, low@350): | 73 | 100-350: | 7.1 | 3.4 | 0.4 | 0.2 |
|  | Total: 149 | p-value: | 0.28 | 0.03 | 0.06 | 0.03 |

Table 2C shows the same cancer related factors as Table 1C but this time showing the relationship with FT levels. When the patients are stratified according to FT level the correlation of GS primary to FT levels is much more significant. Low FT is associated with increased GS. This is weakly apparent in the GS total as well. T3/t2 is also associated with low FT where the individuals with the lowest FT values are associated with the more advanced t3 grade cancers. The FT measurements are also strongly associated with the margins score where low FT shows a statistically significant association with a higher margins score.

Table 3 presents pertinent an earlier version of the entire data set shown in Tables 1 and 2 with some different factors being measured. Men with lowFT ≤5.1 (N=16) were compared to men with normal FT ≥5.1 (N=49). Both pre and postoperative findings are presented. Patient characteristics were similar except men with lowFT and TT <300 were significantly older. Two of the lowFT group recovered sexual function and the normalFT group had a five-fold increased rate of recovery at 15 and 24 months (all p ≤0.02). Multivariate analysis demonstrated both age and lowFT significantly impacted potency; however, lowFT was more significant.

TABLE 2C

|  | Samples | FT group | GS: tot | GS: prim | t3 vs t2 | MARGINS |
|---|---|---|---|---|---|---|
| FT- | 115 | 4.9-12: | 7.0 | 3.3 | 0.3 | 0.1 |
| (hi, low@4.9): | 34 | 2-4.9: | 7.1 | 3.6 | 0.4 | 0.2 |
|  | Total: 149 | p-value: | 0.30 | 0.004 | 0.52 | 0.04 |
| FT | 106 | 5.1-12: | 7.0 | 3.3 | 0.3 | 0.1 |
| (hi, low@5.1): | 43 | 2-5.09: | 7.1 | 3.4 | 0.3 | 0.2 |
|  | Total: 149 | p-value: | 0.51 | 0.15 | 0.49 | 0.05 |
| FT- | 100 | 5.3-12: | 7.0 | 3.3 | 0.3 | 0.1 |
| (hi, low@5.3): | 49 | 2-5.3: | 7.1 | 3.4 | 0.3 | 0.2 |
|  | Total: 149 | p-value: | 0.29 | 0.09 | 0.47 | 0.04 |
| FT- | 78 | 6-12: | 6.9 | 3.2 | 0.2 | 0.1 |
| (hi, low@6): | 71 | 2-6: | 7.1 | 3.5 | 0.4 | 0.2 |
|  | Total: 149 | p-value: | 0.13 | 0.01 | 0.01 | 0.09 |

We did not find TT <300 or LowFT predicted lower baseline characteristics overall. However, men with lowFT in distinction to TT <300 levels had statistically diminished return of potency. These data suggest that independent of patient characteristics and surgical technique, lowFT contributes to postoperative impotence.

TABLE 3

|  | Low FT | Normal FT | p-value | TT <300 | TT >300 | p-value |
|---|---|---|---|---|---|---|
| N | 16 | 49 |  | 36 | 85 |  |
| Age | 64.4 | 58.4 | ≤.01 | 62.8 | 59.5 | 0.01 |
| Pre Operative |  |  |  |  |  |  |
| PSA | 7.0 | 5.3 | .13 | 5.6 | 6.3 | .45 |
| AUA | 10.1 | 8.3 | .37 | 7.8 | 8.0 | .90 |
| Bother | 1.6 | 1.5 | .88 | 1.6 | 1.6 | .93 |
| IIEF-5 | 22.8 | 20.7 | .23 | 22.4 | 21.2 | .25 |
| BNS | 85% | 82% | .24 | 84% | 83% | .33 |
| BMI | 28.1 | 26.4 | .32 | 27.7 | 27.1 | .69 |
| Prostate Weight | 51.8 | 50.3 | .75 | 51.2 | 51.5 | .93 |
| Post Operative |  |  |  |  |  |  |
| PDE-5 qD** (Mos.) | 7.6 | 8.5 | .70 | 7.8 | 8.o | .89 |
| Ave Follow-up | 23.2 | 21.9 | .76 | 21.3 | 22.8 | .67 |
| Total T | 279 | 387 | ≤.01 | 238 | 448 | ≤.01 |
| Potent 3 M | 1/16 (6%) | 10/50 (20%) | .27* | 4/35 (11%) | 14/81(18%) | .33 |
| 15 M | 2/13 (15%) | 21/39 (54%) | .02* | 7/26 (27%) | 20/55 (36%) | .41 |
| 24 M | 2/9 (22%) | 22/31 (71%) | .02* | 9/18 (50%) | 24/45 (53%) | .81 |

Table 4 presents a more complete analysis of return to potency for the entire data set as related to FT. For this analysis it was found most useful to divide the population into three groups: Low FT <5.1 ng/dl (4.5 ng/dl calculated average); Medium FT ≥5.1 ng/dl (6.9 ng/dl calculated average); and High FT >9.05 ng/dl (10.7 ng/dl calculated average). The percentage values show the percentage of each subgroup that reached potency (shown graphically in FIG. 1). The right hand column shows statistical significance (* indicates that the calculation was by the Fischer's exact test.

TABLE 4

|  | Low FT |  | Normal FT |  | High FT |  | p-value |
|---|---|---|---|---|---|---|---|
| N | 37 | 23% | 99 | 61% | 25 | 15.5% |  |
| FT ranges | ≤5.09 |  | 5.1-9.05 |  | ≥9.1 |  |  |
| Potent$^a$ 3 M | 2/37 | 6% | 22/99 | 22% | 7/25 | 28% | .001* |
| 6 M | 2/23 | 9% | 18/58 | 31% | 10/16 | 63% | <.001* |
| 9 M | 7/31 | 23% | 37/85 | 44% | 12/18 | 67% | .01 |
| 15 M | 7/27 | 26% | 39/74 | 53% | 11/16 | 69% | .013 |
| 24 M | 7/23 | 30% | 41/57 | 71% | 12/12 | 100% | <.0001 |

FIG. 1 is a graphic representation of the data in Table 4. The FIGURE shows time to returned potency after RARP with High, FT (>9.05) Medium FT (≥5.1 but <9.0), and Low, FT (<5.1); for men with preoperative IIEF-5s>21 within all ages. P-values were significant at p=0.03, 0.004, 0.009, 0.01, and ≤0.0001 for 3, 6, 9, 15, and 24 months respectively.

Testosterone, for reasons that have not been clearly defined, drops to below normal levels in nearly 45% of the male population over the age of 45. Sexual dysfunction and decreased libido has been tied to low levels of testosterone. There is also evidence that there are testosterone receptors in the nerve responsible for erections. Clearly, higher levels of testosterone result in improved recovery of potency following prostate surgery. We believe that a fundamental principle is that a hidden cause for failure to recover sexual function following surgery is low testosterone which does not allow the nerve to recover normally.

Therefore men with either low or low normal testosterone levels can be treated with testosterone (or other androgens such as synthetic steroids structurally related to testosterone) to prevent, mitigate or treat erectile dysfunction associated with RARP/RP. A large number of testosterone replacement drugs such as Androgel can easily be given to appropriate patients prior to or even following surgery. The amount of testosterone administered is sufficient to raise the free testosterone level into the high free testosterone range as defined above (generally greater than about 9 ng/dl). Where other androgens are used, the equivalent effectiveness of each different molecule in terms of testosterone is generally known. Sufficient androgen is given so that the effectiveness of the circulating level of androgen plus testosterone falls within the high free testosterone range. As will be clear to those of ordinary skill in the art, the testosterone or other androgen is administered at the usual amount and frequency. Circulating testosterone levels are measured at appropriate intervals (i.e., weekly or monthly) and the dosage adjusted if necessary.

The present invention can be used in a predictive manner where patients presenting with low testosterone levels (particularly low FT) should be carefully evaluated to the presence of more extensive and more aggressive cancers. Because low testosterone levels predict prolonged recovery of sexual functioning, particular care should be made to spare low testosterone patents from surgical damage. Methods such as hypothermic surgery might be particularly beneficial for these patients. On the other hand, patients presenting with high testosterone levels will be expected to have less aggressive cancer and will be expected to recover more fully and more quickly.

At this time anecdotal results support the idea that supplementing low testosterone levels leads to more rapid and more complete recovery. There are limited data indicating that this supplementation does not lead to recurrence of the cancer. We believe that preoperative supplementation will produce even more dramatic improvements. However, such studies must be undertaken with caution because there is a possibility that the higher grade cancers expected in low testosterone individuals may be stimulated by testosterone supplementation. A risk benefit analysis suggests that a relatively brief (1-2 months) preoperative supplementation is not likely to cause significant problems at least in individuals where the cancer has not escaped from the prostate. The preferred treatment is to administer sufficient testosterone to bring FT levels into the high FT range as illustrated in FIG. 1. In addition to the 1-2 month preoperative treatment, postoperative supplementation should be continued until potency has returned.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

1. Rhoden E L, Morgentaler A. Risks of testosterone-replacement therapy and recommendations for monitoring. N Engl J Med 2004; 350; 482.
2. Raynaud J P. Testosterone deficiency syndrome: Treatment and cancer risk. J Steroid Biochem Mol Biol 2009; 114: 96-105.
3. Morales A, Carson C, Hellstom W, Lipshultz L and Morgentaler A. Feb. 11, 2003 Position statement on Diagnosis, Treatment, and Monitoring of Male Late Onset Hypogonadism by Sexual Medicine Society of North America, Inc., A Specialty Society of the AUA. Available at http://www.smsna.org/about/dtmmloh.asp. Accessed Jul. 2, 2004.
4. Harman S M, Metter E J, Tobin J D, Pearson J, Blackman M R and Baltimore Longitudinal Study of Aging: Longitudinal effects of aging on serum total and free testosterone levels in healthy men. J Clin Endocrinol Metab 2001; 86: 724.
5. Mulligan T, Frick M F, Zuraw Q C, Stemhagen A, McWhirter C. Prevalence of hypogonadism in males aged at least 45 years: the HIM study. Int J Clin Pract 2006; 60: 762-769.
6. Snyder P H, Peachey H, Berlin J A, Hannoush P, Haddad G, Dlewati A, et al. Effects of testosterone replacement in hypogonadal men. J Clin Endocrinol Metab 2000; 85: 2670.
7. Sih R, Morley J E, Kaiser F E, Perry H M. 3rd Patrick P and Ross C. Testosterone replacement in older hypogonadal men: a 12-month-randomized controlled trial. J Clin Endocrinol Metab 1997; 82: 1661.
8. Pope H G Jr, Cohane G H, Kanayama G, Siegel A J and Hudson J I. Testosterone gel supplementation for men with refractory depression: a randomized, placebo-controlled trial. Am J Psychiatry 2003; 160: 105.
9. Huggins C and Hodges C V. Studies on prostate cancer. I. The effect of castration, of estrogen and of androgen injection on serum phosphatases in metastatic prostate carcinoma of the prostate. Cancer Res 1941; 1: 293-7.
10. Morgentaler A. Testosterone therapy for men at risk for or with history of prostate cancer. Curr Treat Options Oncol 2006; 7; 363-9.
11. Kaufman J M and Graydon R J. Androgen replacement after curative radical prostatectomy for prostate cancer in hypogonadal men. J Urol 2004; 172: 920-922.
12. Agarwal P K and Oefelein M G. Testosterone replacement therapy after primary treatment for prostate cancer. J Urol 2005; 173: 533-6.
13. Khera M, Grober E D, Najari B, Colen J S, Mohamed O, Lamb D J and Lipshultz L I. Testosterone replacement therapy following radical prostatectomy. J Sex Med 2009; 6: 1165.
14. Morgentaler A and Rhoden E L. Prevalence of prostate cancer among hypogonadal men with prostate specific antigen levels of 4.0 ng/mL or less. Urology 2006; 68: 1263-7.
15. Hoffman M A, DeWolf W C and Morgentaler A. Is low serum free testosterone a marker for high grade prostate cancer? J Urol 2000; 163: 824-7.
16. Rhoden E L and Morgentaler A. Influence of demographic factors and biochemical characteristics on the prostate-specific antigen (PSA) response to testosterone replacement therapy. Int J Impot Res 2006; 18: 201-5.
17. Thomson Healthcare. 2005 Physicians' desk reference. 59th edition. Montvale, N.J.: Thomson Healthcare; 2005.
18. World Health Organization: 3rd International Consensus Consultation of Prostate Cancer, Paris, France, 2002.
19. Kattan M W, Eastham J A, Stapleton A M, Wheeler T M and Scardino P T. A preoperative nomogram for disease recurrence following radical prostatectomy for prostate cancer. J Natl Cancer Inst 1998; 90:766-71.
20. Ward J F, Blute M L, Slezak J, Bergstralh E J and Zincke H. The long-term clinical impact of biochemical recurrence of prostate cancer 5 or more years after radical prostatectomy. J Urol 2003; 170: 1872-6.
21. Bhasin S, Cunningham G R, Hayes F J, Matsumoto A M, Snyder P J, Swerdloff R S, Montori V M. Testosterone therapy in adult men with androgen deficiency syndromes: an endocrine society clinical practice guideline. J Clin Endocrinol Metab 2006; 91:1995-2010.
22. Wang C, Nieschlag E, Swerdloff R, Behre H M, Hellstrom W J, Gooren L J, et al. ISA, ISSAM, EAU, EAA and ASA recommendations: investigation, treatment and monitoring of late-onset hypogonadism in males. Int J Impot Res 2009; 21: 1-8.
23. Rhoden E L and Morgentaler A. Risks of testosterone-replacement therapy and recommendations for monitoring. N Engl J Med 2000; 56: 899.

What is claimed is:

1. A method for estimating the likelihood that a patient undergoing radical prostatectomy will recover sexual potency comprising the steps of:
   measuring total and free testosterone values in a sample of the patient's blood;
   determining if the free testosterone value falls in a high free testosterone, medium free testosterone or low free testosterone range wherein the high free testosterone range is greater than about 9 ng/dl, the medium free testosterone range is greater than or equal to about 5 ng/dl and less than about 9 ng/dl and the low free testosterone range is less than about 5 ng/dl; and
   providing the likelihood of recovering sexual potency where membership in the high free testosterone range indicates a high likelihood of recovering sexual potency, membership in the middle free testosterone range indicates a moderate likelihood of recovering sexual potency and membership in the low free testosterone range indicates a lower likelihood of recovering sexual potency.

2. A method of enhancing the recovery of sexual potency of a patient following radical prostatectomy surgery comprising the steps of:
   measuring total and free testosterone values in a sample of the patient's blood;

determining if the free testosterone value falls in a high free testosterone, medium free testosterone or low free testosterone range wherein the high free testosterone range is greater than about 9 ng/dl, the medium free testosterone range is greater than or equal to about 5 ng/dl and less than about 9 ng/dl and the low free testosterone range is less than about 5 ng/dl; and if the free testosterone value falls in the medium or low free testosterone range administering sufficient testosterone to increase the free testosterone level into the high free testosterone range.

3. The method according to claim 2 wherein sufficient androgen is administered to result in an effective testosterone level into the high free testosterone level.

4. The method according to claim 2, wherein the free testosterone level is increased prior to surgery.

5. The method according to claim 2, wherein the free testosterone level is increased after surgery.

6. A method of enhancing the recovery of sexual potency of a patient following radical prostatectomy surgery comprising the steps of providing therapy to increase free testosterone values of the patient.

7. The method according to claim 6, wherein the free testosterone level is increased prior to surgery.

8. The method according to claim 6, wherein the free testosterone level is increased after surgery.

9. The method according to claim 6, wherein the free testosterone level is increased to a level of greater than about 9 ng/dl.

\* \* \* \* \*